US 9,237,933 B2

(12) United States Patent
Agbodoe et al.

(10) Patent No.: US 9,237,933 B2
(45) Date of Patent: Jan. 19, 2016

(54) UNIVERSAL ARM SYSTEM

(75) Inventors: Victor Agbodoe, Raynham, MA (US); Olaf Storz, Emmingen (DE)

(73) Assignee: Specialty Surgical Instrumentation Inc., Antioch, TN (US)

( * ) Notice: Subject to any disclaimer, the term of this patent is extended or adjusted under 35 U.S.C. 154(b) by 95 days.

(21) Appl. No.: 13/314,973

(22) Filed: Dec. 8, 2011

(65) Prior Publication Data

US 2013/0099081 A1 Apr. 25, 2013

Related U.S. Application Data

(60) Provisional application No. 61/550,198, filed on Oct. 21, 2011.

(51) Int. Cl.
*E04G 3/00* (2006.01)
*A61B 19/00* (2006.01)
*F16M 11/40* (2006.01)

(52) U.S. Cl.
CPC ............. *A61B 19/26* (2013.01); *F16M 11/40* (2013.01); *A61B 2019/266* (2013.01); *A61B 2019/268* (2013.01)

(58) Field of Classification Search
CPC .......................... F16M 13/022; A61B 19/26
USPC .............. 248/288.51, 288.31, 288.11, 104; 248/181.1, 181.2, 276.1, 296.1, 316.4, 160; 606/66, 287
See application file for complete search history.

(56) References Cited

U.S. PATENT DOCUMENTS

| | | | |
|---|---|---|---|
| 2,533,494 A * | 12/1950 | Mitchell, Jr. .............. | 248/160 |
| 4,254,763 A | 3/1981 | McCready | |
| 4,424,724 A | 1/1984 | Bookwalter | |
| 4,949,927 A * | 8/1990 | Madocks et al. ........ | 248/276.1 |
| 5,375,481 A | 12/1994 | Cabrera | |
| 5,513,827 A * | 5/1996 | Michelson ............... | 248/279.1 |
| 5,560,728 A | 10/1996 | McFadden | |
| 6,007,486 A * | 12/1999 | Hunt et al. ............... | 600/205 |
| 6,306,146 B1 | 10/2001 | Dinkler | |
| 6,558,407 B1 | 5/2003 | Ivanko | |
| 6,730,020 B2 | 5/2004 | Peng et al. | |
| 6,732,988 B2 | 5/2004 | Ihalainen | |
| 6,758,809 B2 | 7/2004 | Briscoe | |
| 6,808,493 B1 * | 10/2004 | Bookwalter et al. ..... | 600/233 |
| 7,717,844 B2 | 5/2010 | Cohn | |
| 7,794,387 B2 | 9/2010 | Olson | |
| 2001/0025905 A1 * | 10/2001 | Carpenter et al. ........ | 248/160 |
| 2002/0177754 A1 | 11/2002 | Phillips | |
| 2006/0025810 A1 | 2/2006 | Shelton | |
| 2013/0082157 A1 * | 4/2013 | Agbodoe et al. .......... | 248/315 |

FOREIGN PATENT DOCUMENTS

EP 1972264 A1 9/2008
WO 02085187 A2 10/2002

* cited by examiner

*Primary Examiner* — Kimberly Wood
(74) *Attorney, Agent, or Firm* — Hayes Soloway, P.C.

(57) ABSTRACT

A universal arm has a proximal end, a distal end and a middle portion therebetween. The middle portion has a plurality of interconnected ball and socket pieces. A plurality of clamps are selectively fixedly connected to the distal end of the universal arm by a connection that permits the selective rotation of each one of the plurality of clamps by 360° with respect to the distal end of the universal arm.

15 Claims, 8 Drawing Sheets

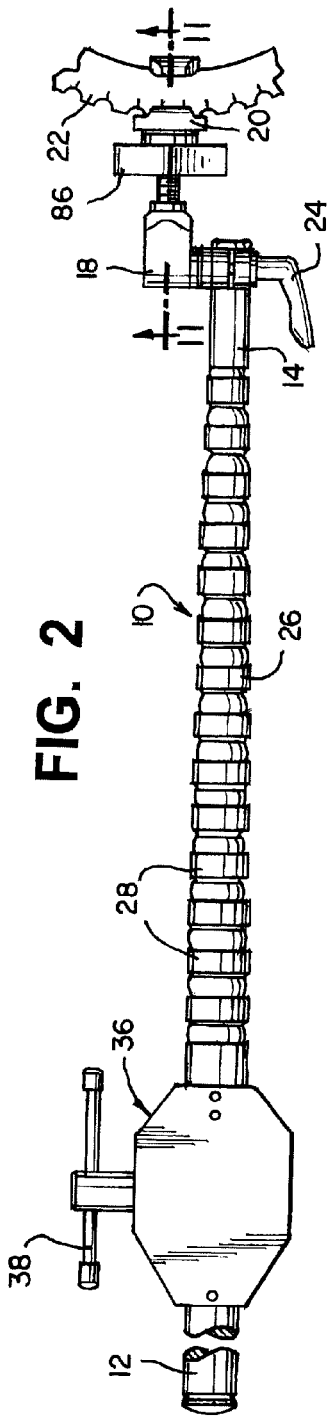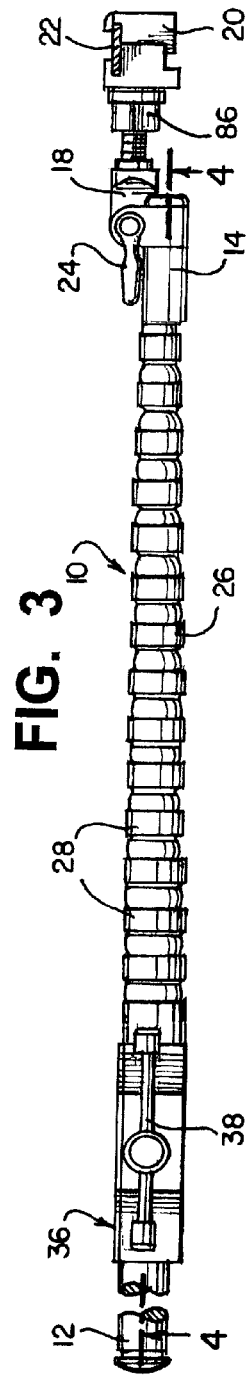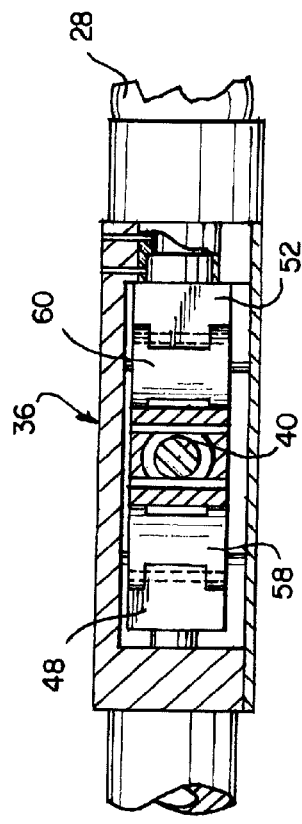

FIG. 9
FIG. 10
FIG. 11 A
FIG. 11 B
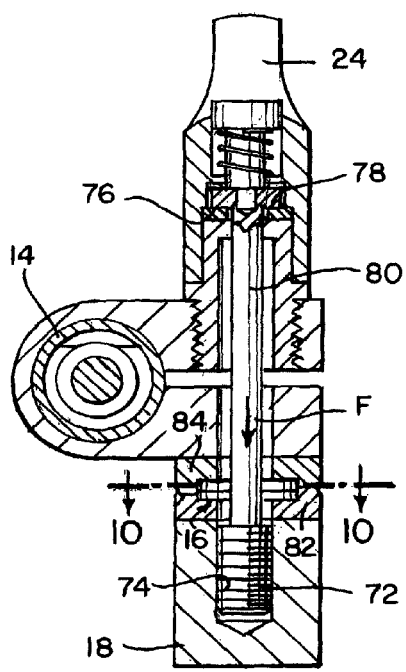
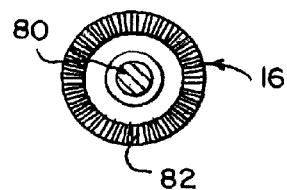
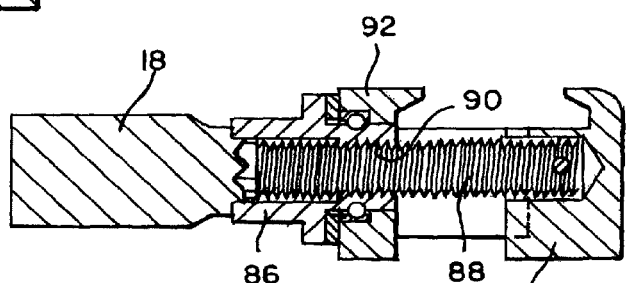
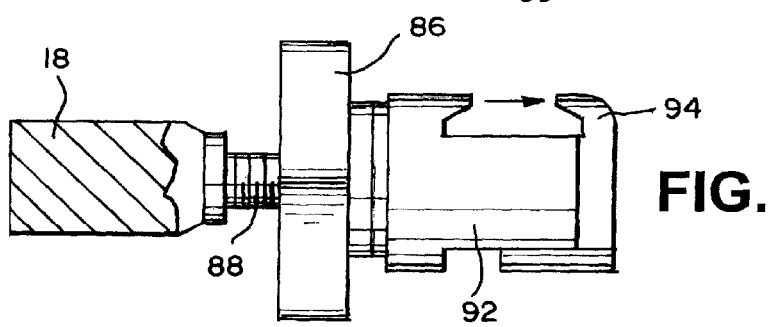

UNIVERSAL ARM SYSTEM

CROSS REFERENCE TO RELATED APPLICATION

This application claims priority benefit to U.S. Provisional Application No. 61/550,198 filed Oct. 21, 2011.

FIELD OF THE INVENTION

The present invention relates to methods and devices for universal arm system.

BACKGROUND OF THE INVENTION

During surgery, retractors, such as those found in the BOOKWALTER™ refractor kit, which is commercially available from Codman & Shurtleff, Inc. of Raynham, Mass., are often used to assist the surgeon and other operating room personnel to provide exposure to the surgical site for a broad range of surgical procedures. In surgical operations of the chest or abdomen, for example, it is often necessary to use a retraction apparatus to retain tissue away from the operative site. Typically, the retraction apparatus includes a housing member configured to lock onto a circumferential ring 10 located above the operative site (see FIGS. 1A and 1B). A retraction blade can usually be found for grabbing the tissue around the surgical incision. The housing member can also include a ratcheting mechanism and/or a tilting mechanism to draw the retraction blade away from the incision, thereby effecting the pulling away and/or lifting of the tissue around the incision to expose the desired surgical area. Examples of such retractor systems are disclosed in U.S. Pat. Nos. 4,254, 763, 4,424,724, 5,375,481 and 6,808,493, the disclosures of which are hereby incorporated by reference in their entirety. During open surgical operations, such as, for example, open bariatric, ALIF procedures, hepatic resections, transplant procedures, abdominal aortic aneurysms, hernia repair, appendectomy and others, many different instruments are used, such as, for example, a retractor blade with ring attachment systems are used. In some medical procedures, other instruments, such as, for example, cameras, laparoscopic instruments, fiber optic cables, are also used in the surgical area. These instruments typically are used so that their distal end is located in the surgical site. The instrument has a clamp on its proximal end. The instrument is connected to a post adjacent to the surgical area. However, in many instances, the location of the post is not in a convenient location for the surgeon at the operating site. Thus, there is a need for a system that can securely hold a number of different instruments at a convenient location for the surgeon at the operating site. The system should be adjustable and sufficiently strong to carry the load from the instrument. The system includes an adjustable arm that bend with one curve or a double curve.

SUMMARY OF THE INVENTION

A universal arm has a proximal end, a distal end and a middle portion therebetween. The middle portion has a plurality of interconnected ball and socket pieces. A plurality of clamps are selectively fixedly connected to the distal end of the universal arm by a connection that permits the selective rotation of each one of the plurality of clamps by 360° with respect to the distal end of the universal arm.

BRIEF DESCRIPTION OF THE DRAWINGS

The invention will be more fully understood from the following detailed description taken in conjunction with the accompanying drawings, in which:

FIG. 2 is a top view of the universal arm in accordance with the present invention;

FIG. 3 is a side view of the universal arm in accordance with the present invention;

FIG. 3 is an exploded view of the ring holder and the sets of ring pairs;

FIG. 6 is a cross-sectional view taken along line 6-6 of FIG. 4A and looking in the direction of the arrows;

FIG. 9 is cross-sectional view taken along line 9-9 of FIG. 4A and looking in the direction of the arrows;

FIG. 10 is cross-sectional view taken along line 10-10 of FIG. 9 and looking in the direction of the arrows;

FIG. 11A is a partial cross-sectional view, with parts broken away, showing the retractor ring holder;

FIG. 11B is a side view of the retractor ring holder;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
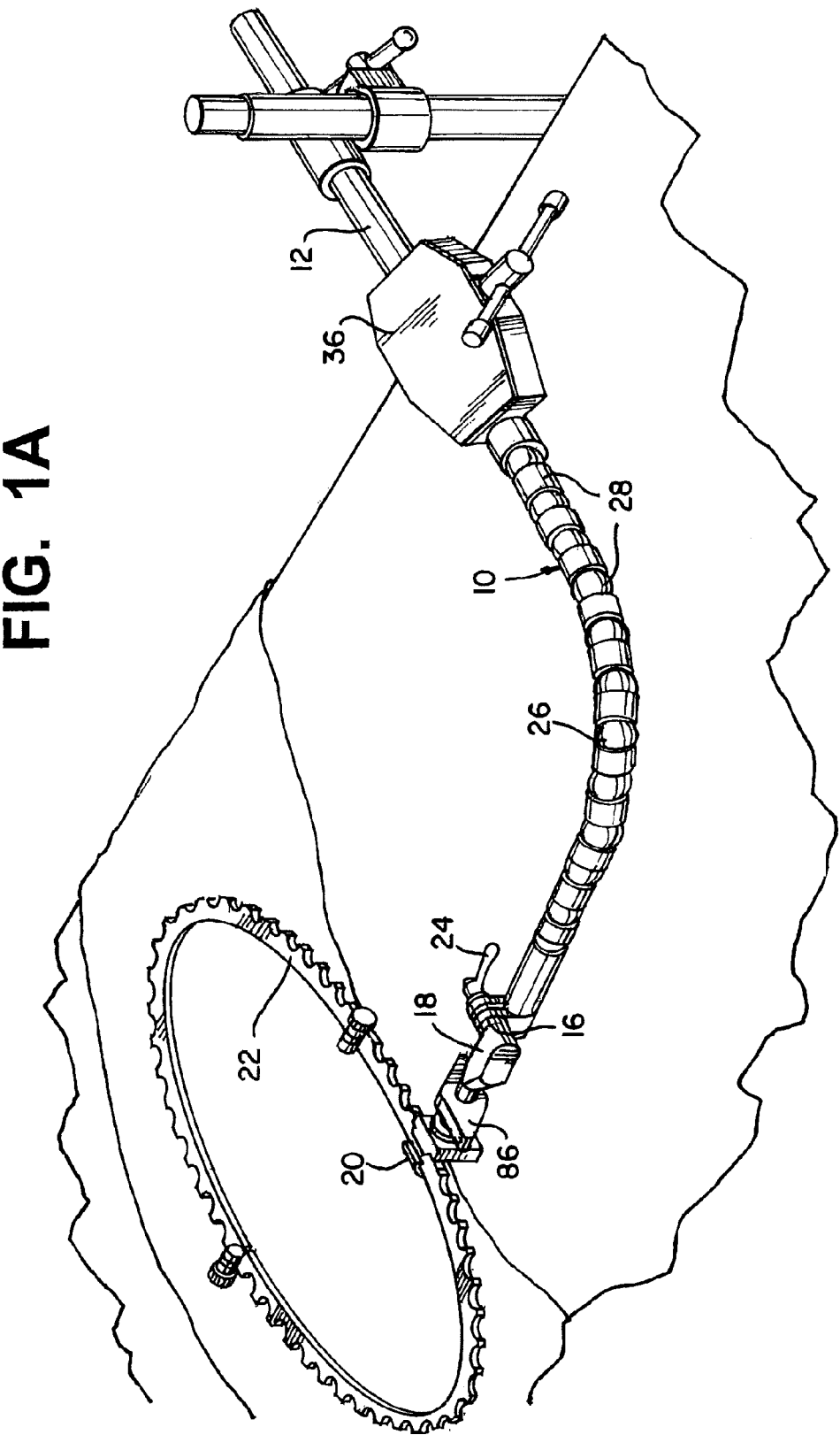
FIGS. 1A and 1B are plan views of a universal arm being used to hole a retractor ring.
Figure 1B:
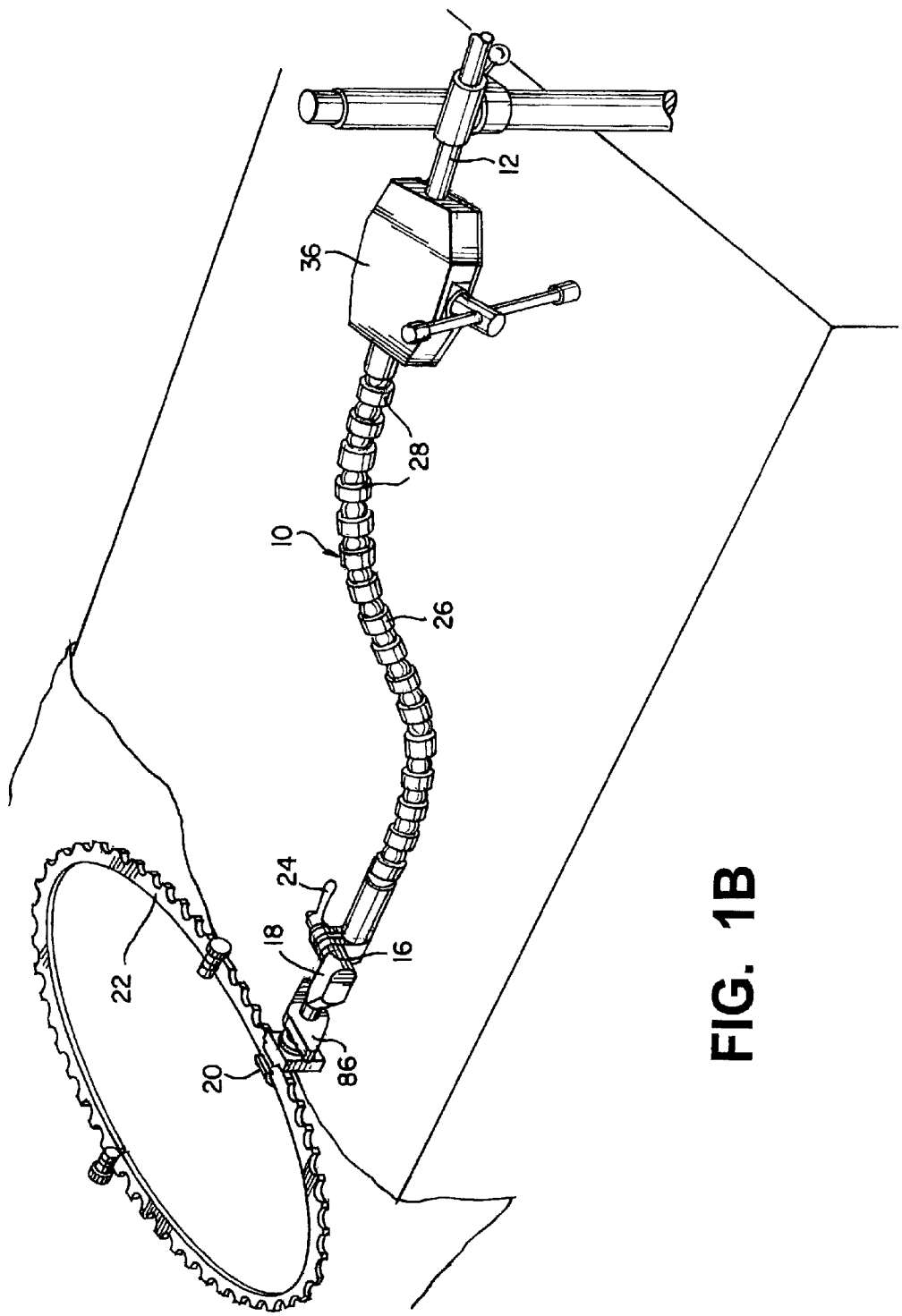
Figure 4A:
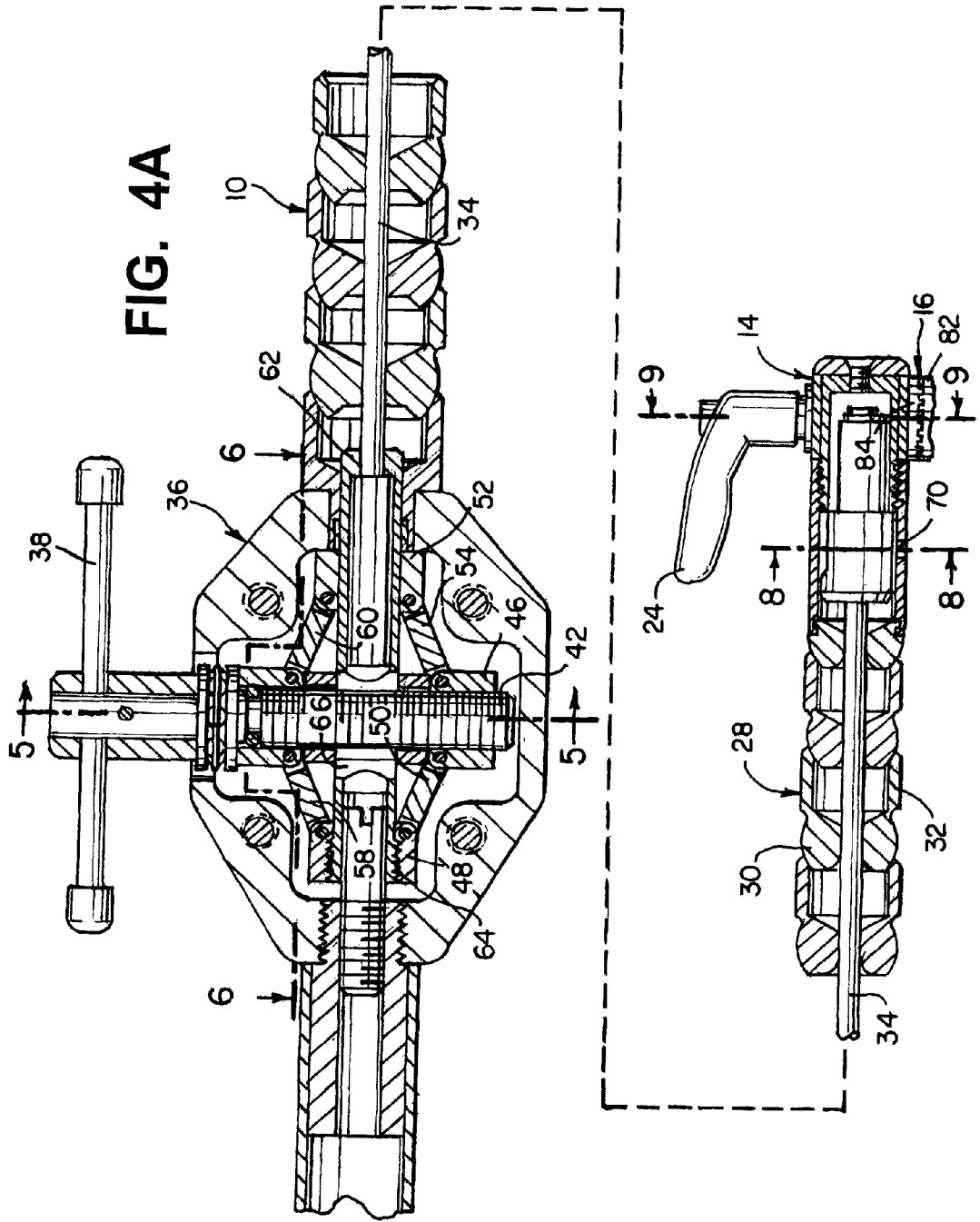
FIG. 4A is a cross-sectional view, with parts broken away, of a portion of the universal arm in accordance with the present invention.
Figure 4B:
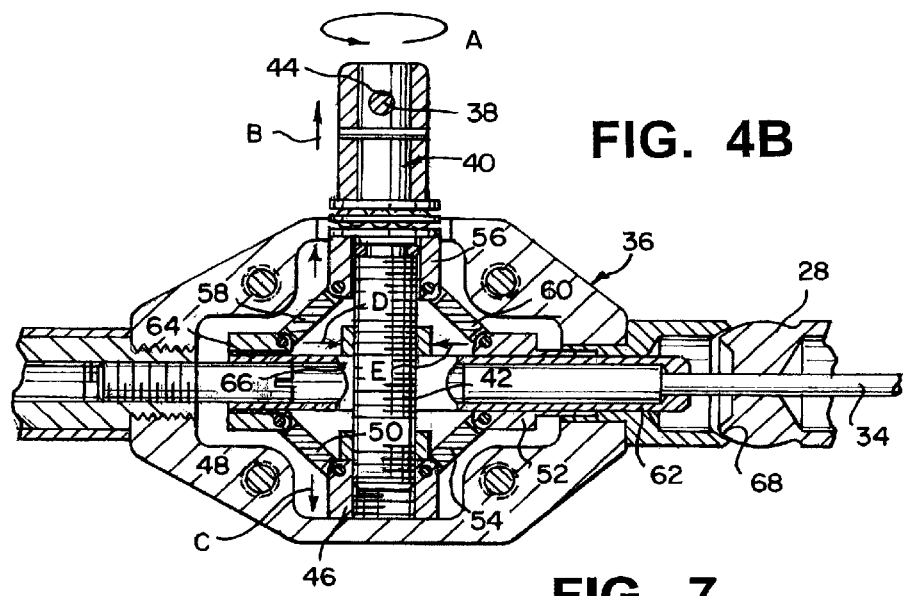
FIG. 4B is a cross-sectional view, with parts broken away, of a portion of the universal arm in accordance with the present invention.
Figure 5:
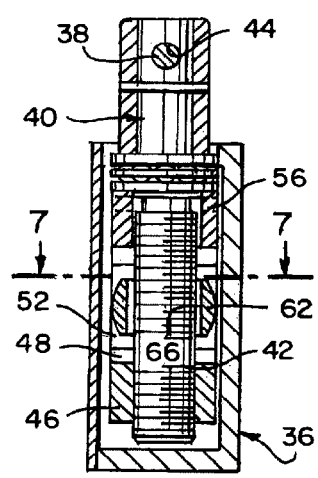
FIG. 5 is a cross-sectional view taken along line 5-5 of FIG. 4A and looking in the direction of the arrows.
Figure 7:
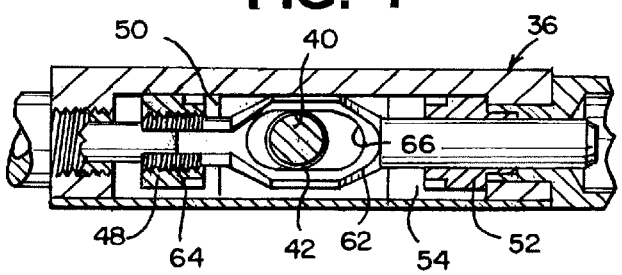
FIG. 7 is a cross-sectional view taken along line 7-7 of FIG. 5 and looking in the direction of the arrows.

The present invention provides methods and devices for a universal arm for holding a number of different instruments at a convenient location for the surgeon at the operating site. Referring now to FIGS. 1A and 1B, a universal arm 10 is illustrated. Universal arm 10 has a proximal end 12 and a distal end 14 as shown in FIGS. 2 and 3. Distal end 14 has an annual mating serrated saw-like connection 16, which may also be referred to as a starburst connection. Various tools can be connected to starburst connection 16. As shown in FIGS.

1A-3, a retractor ring holder 18 is connected to the universal arm 10 via the starburst connection. Ring holder 18 has an adjustable clamp 20 to selectively connect and rigidly hold a retractor ring 22. A rotatable handle 24 is provided at the distal end 14 of the universal arm 10. Handle 24 is rotated in one direction to loosen the connection between the universal arm 10 and the ring holder 18 so that the desired position of the ring holder can be achieved. Once the desired position is obtained, the user may rotate handle 24 in the opposite direction to engage the annual mating serrated saw-like connection 16 and thereby fix the location of ring holder 18 or any of the other tools, which are shown in FIGS. 11-14B.

Referring now to FIGS. 2-7, the middle portion 26 of universal arm 10 includes a plurality of ball and socket pieces 28. As can be seen in FIGS. 4A and 4B, each ball and socket piece 28 has a ball end 30 and a socket, or ball receiving end, 32. A cable 34 passes through each ball and socket piece 28. Cable 34 is moveable by a handle mechanism 36 between a locked position as shown in FIG. 4A and an unlocked or adjustable position as shown in FIG. 4B. Handle mechanism 36 includes a handle 38 that is received in a through bore 44 of a shaft 40. Shaft 40 includes an externally threaded portion 42. A movable transversable bearing 46 has in internally threaded surface that mate with the externally threaded portion 42. Bearing 46 is pivotally connected to a movable longitudinal bearing 48 by a linkage bar 50. Similarly, bearing 46 is pivotally connected to a fixed longitudinal bearing 52 by a linkage bar 54. Both the movable longitudinal bearing 48 and the fixed longitudinal bearing 52 are pivotally connected to a fixed transversal bearing 56 by a linkage bar 58, 60, respectively. Rotation of handle 38 in the direction indicated by arrow A in FIG. 4B will cause shaft 40 to move in the direction indicated by arrow B and will cause movable transversable bearing 46 to move in the direction indicated by arrow C, which causes movable longitudinal bearing 48 to move in the direction indicated by arrow D and the fixed longitudinal bearing 52 to move in the direction indicated by arrow E. Movable longitudinal bearing 48 is fixedly connected to a slotted rod 62 by an internally threaded connection 64. Because slotted rod 62 is fixedly connected to movable longitudinal bearing 48, slotted rod 62 will move in the direction indicated by arrow D when movable longitudinal bearing 48 moves in the direction indicated by arrow D. Slotted rod 62 has a slot 66 to receive rod 40. The opposite end of slotted rod 62 is fixedly connected to cable 34. Thus, when slotted rod 62 moves in the direction indicated by arrow D, cable 34 will also move in the direction indicated by arrow D, thereby causing the plurality of ball and socket pieces 28 to loosen each ball and socket piece 28 as indicated by the space 68 between each ball and socket piece 28 in FIG. 4B. The user can then adjust the position of the universal arm to any desired position, including a single bend, as shown in FIG. 1A, or a double bend, or s-curve as shown in FIG. 1B. Once the universal arm is in the desired position, the user can rotate handle so that the shaft rotates in the opposite direction of Arrow A to quickly move the universal arm from the unlocked, or adjustable position to the locked position. Because of the linkage shown in FIGS. 4A-7, a relatively strong and rigid universal arm can be achieved to hold various tools and instruments on the distal end 14 of the universal arm 10.

Figure 8:
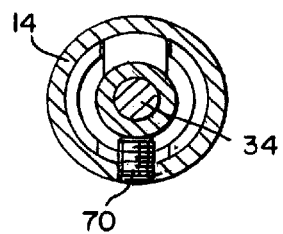
FIG. 8 is cross-sectional view taken along line 8-8 of FIG. 4A and looking in the direction of the arrows.

Referring now to FIG. 8, the distal end 14 of the universal arm 10 is shown. Cable 34 is fixedly connected to the distal end 14 by a set screw 70.

Referring now to FIG. 9, the distal end 14 of universal arm 10 is illustrated. Distal end 14 includes a shaft 80 that has a threaded rod portion 72 so that a number of different clamps or other instruments can be selectively fixedly connected to the universal arm 10. In this illustration, a retractor ring holder 18 is shown connected to the distal end 14 of the universal arm. The retractor ring holder 18 has a blind threaded bore 74 that mate with threaded rod 72 to selectively fixedly connect retractor ring holder 18 to the universal arm 10. Once connected, the user can rotate handle 24, to cause mating cam surfaces 76, 78 to cause shaft 80 to move in the direction indicated by arrow F to move annular serrated ring 82 of the ring holder 18 away from the annular serrated ring 84 of the distal end 14 of universal arm 10, thereby permitting the starburst connection 16 to be in the adjustable position. The user can then rotate the retractor ring holder 18 360° with respect to the distal end 14 of universal arm 10 to any position that is at a convenient location for the surgeon at the operating site. Once the retractor ring holder 18 is in the desired position, the user can then rotate handle 24 in the opposite direction to cause mating cam surfaces 76, 78 to cause shaft 80 to move in the opposite direction indicated by arrow F to move annular serrated ring 82 of the ring holder 18 toward the annular serrated ring 84 of the distal end 14 of universal arm 10, thereby causing the starburst connection 16 to be in the locked position.

Referring now to FIGS. 1A, 1B, 11A and 11B, the retractor ring holder 18 is shown in greater detail. A handle 86 is rotatably connected to retractor ring holder 18 via a threaded shaft 88. Handle 86 has an internally threaded portion 90 that mates with threaded shaft 88. Thus, when handle 86 is rotated clamp arm 92 moves toward or away from clamp arm 94 depending upon which way handle 86 is rotated. As shown in FIGS. 1A and 1B, retractor ring holder 18 can selectively clamp ring 22 in place at a convenient location for the surgeon at the operating site.

Figure 12:
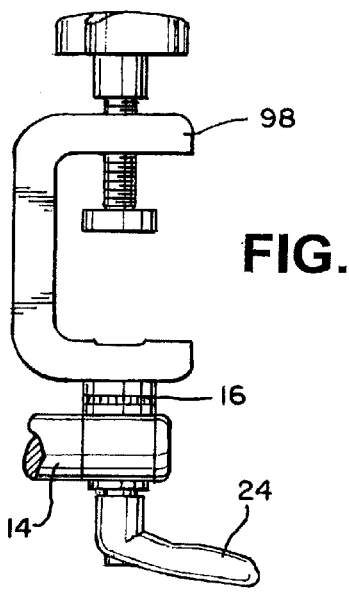
FIG. 12A is a plan view of a clamp in accordance with the present invention.
FIG. 12B is a perspective view of the clamp shown in FIG. 12A holding a camera.
Figure 12:
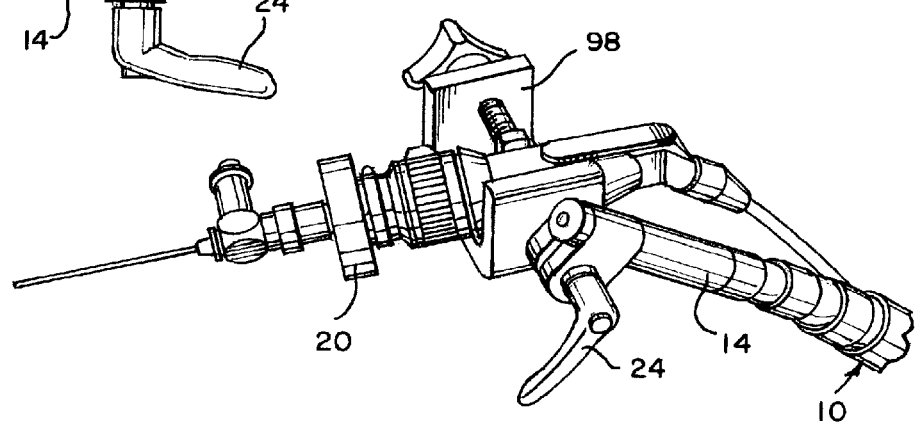
Figure 13:
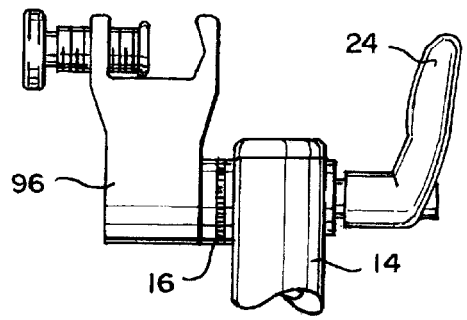
FIG. 13A is a plan view of a clamp in accordance with the present invention.
FIG. 13B is a perspective view of the clamp shown in FIG. 13A holding a laporoscopic tool.
Figure 14:
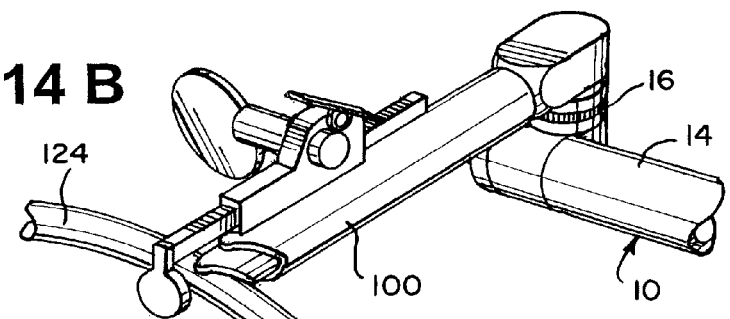
FIG. 14A is a plan view of a spring loaded clamp in accordance with the present invention.
FIG. 14B is a perspective view of the clamp shown in FIG. 14A holding an irrigation tube.
Figure 14:
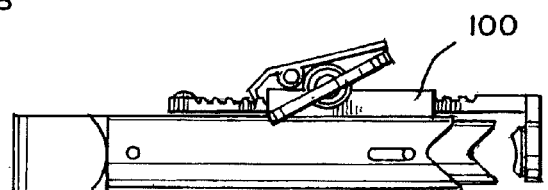
Figure 13:
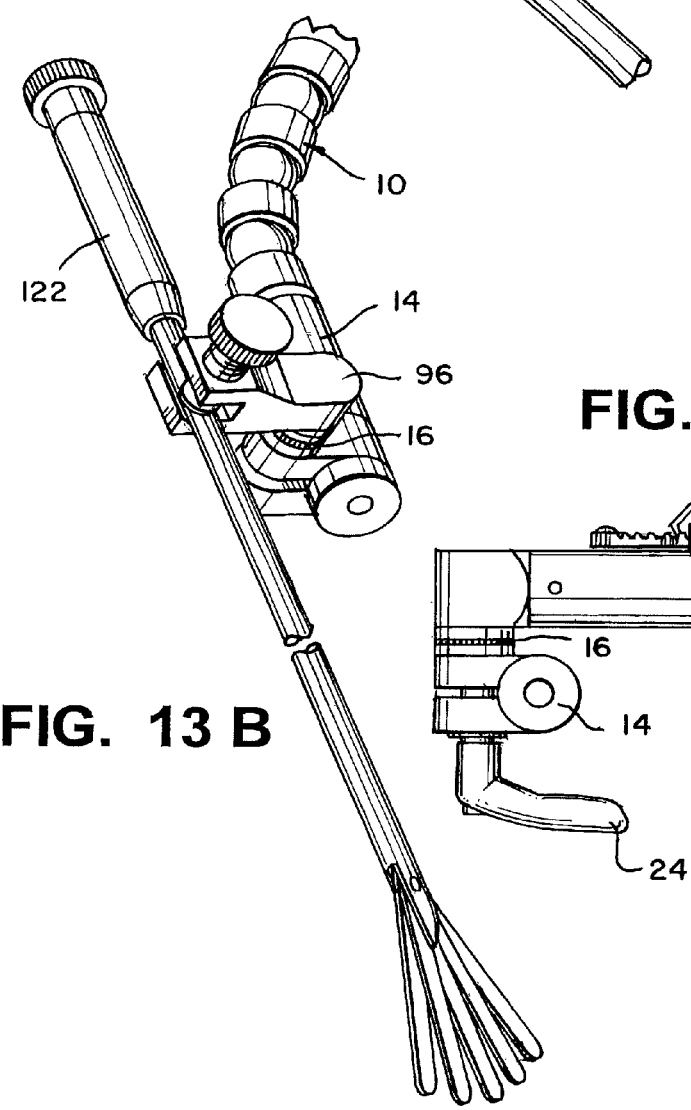

Referring now to FIGS. 12A-14B, additional clamps 96, 98, 100 are illustrated, each of which can be selectively connected to the distal end 14 of the universal arm 10. Each clamp has a blind threaded bore, similar to blind threaded bore 74 of the retractor ring holder 18 that mate with threaded rod 72 to selectively fixedly connect the clamp 96, 98, 100 to the universal arm 10. Each clamp also has an annular serrated ring 82', 82'', 82''', similar to ring 82 of the ring holder 18 to mate with annular serrated ring 84 to form a starburst connection 16', 16'', 16'''. FIGS. 12A and 12B show a relatively large clamp 98 that can be used, for example, to hold a camera 120 at a convenient location for the surgeon at the operating site. FIGS. 13A and 13B show a relatively small clamp 96 that can be used, for example, to hold a laparoscopic instrument 122 at a convenient location for the surgeon at the operating site. FIGS. 14A and 14B show a spring loaded clamp 100 that can be used, for example, to hold a fiber optic cable 124 or an irrigation tube at a convenient location for the surgeon at the operating site. Spring loaded clamp 100 includes a handle 102. Rotation of handle 102 causes bar 104 to move in the direction indicated by arrow G. A pawl lever mechanism 110 is spring biased into contact with a plurality of pawls 112 on the upper surface of bar 104. The pawl mechanism permits bar 104 to move in the direction indicated by arrow G, but not in the opposite direction. Thus, jaw 100 is moved closer to fixed jaw 108 into the desired position to hold, for example, a fiber optic cable at a convenient location for the surgeon at the operating site. To release the fiber optic cable, or other tool, the user depresses on the pawl lever 110 at end 114 in the direction indicated by arrow H to overcome the spring pressure created by a spring 118 to move the opposite end 116 from engagement with the pawls 112.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A universal arm assembly comprising:
   a universal arm having a proximal end, a distal end and a middle portion therebetween, the middle portion having a plurality of interconnected ball and socket pieces;
   at least one clamp fixedly connected to the distal end of the universal arm by a connection joint, wherein the connection joint permits selective rotation of the at least one clamp by 360° with respect to the distal end of the universal arm;
   a cable extending through each of the plurality of interconnected ball and socket pieces; and
   a handle mechanism having at least one shaft connected to an end of the cable, wherein the at least one shaft is positioned substantially perpendicular to a length of the end of the cable, whereby a position of at least the end of the cable is movable relative to the at least one shaft based on a rotational movement of the at least one shaft, wherein the at least one shaft is connected to the end of the cable with at least one movable bearing threadedly engaged with the at least one shaft, at least one fixed bearing connected to the end of the cable, and at least one linkage connected between the at least one movable bearing and the at least one fixed bearing.

2. The universal arm assembly according to claim 1, wherein the cable is moveable between a locked position and an adjustable position.

3. The universal arm assembly according to claim 2, further comprising a rotatable handle connected to the at least one shaft.

4. The universal arm assembly according to claim 2, wherein in the adjustable position the plurality of ball and socket pieces have a space between each ball and socket piece.

5. The universal arm assembly according to claim 4, wherein in the locked position the plurality of ball and socket pieces have no space between each ball and socket piece.

6. The universal arm assembly according to claim 1, wherein the at least one clamp further comprises a retractor ring holder and a clamp.

7. The universal arm assembly according to claim 6, wherein the at least one clamp is a spring loaded clamp.

8. The universal arm assembly according to claim 1, wherein the at least one linkage is pivotally connected between the at least one movable bearing and the at least one fixed bearing.

9. A universal arm assembly comprising:
   a universal arm having a proximal end, a distal end and a middle portion therebetween, the middle portion having a plurality of interconnected ball and socket pieces;
   at least one clamp fixedly connected to the distal end of the universal arm by a connection joint, wherein the connection joint permits selective rotation of the at least one clamp by 360° with respect to the distal end of the universal arm;
   a cable extending through each of the plurality of interconnected ball and socket pieces; and
   a handle mechanism having at least one shaft connected to an end of the cable, wherein the at least one shaft is positioned substantially perpendicular to a length of the end of the cable, whereby a position of at least the end of the cable is movable relative to the at least one shaft based on a rotational movement of the at least one shaft, wherein the at least one shaft is connected to the end of the cable with at least two fixed bearings connected together with at least one linkage, wherein a first fixed bearing is connected to the at least one shaft and a second fixed bearing is connected to the end of the cable.

10. A universal arm assembly comprising:
    a universal arm having a proximal end, a distal end and a middle portion therebetween, the middle portion having a plurality of interconnected ball and socket pieces;
    at least one clamp fixedly connected to the distal end of the universal arm by a connection joint, wherein the connection joint permits selective rotation of the at least one clamp by 360° with respect to the distal end of the universal arm;
    a cable extending through each of the plurality of interconnected ball and socket pieces; and
    a handle mechanism having at least one shaft connected to an end of the cable, wherein the at least one shaft is positioned substantially perpendicular to a length of the end of the cable, whereby a position of at least the end of the cable is movable relative to the at least one shaft based on a rotational movement of the at least one shaft, wherein the handle mechanism further comprises a slotted rod connected between the end of the cable and a threaded anchor, wherein the at least one shaft is positioned within a slot of the slotted rod, wherein the slotted rod is positioned substantially perpendicular to a length of the at least one shaft.

11. The universal arm assembly according to claim 10, wherein the slotted rod is connected to the threaded anchor with at least one threaded movable bearing.

12. The universal arm assembly according to claim 1, wherein the connection joint permits selective rotation of the at least one clamp by 360° in at least two planes with respect to the distal end of the universal arm.

13. The universal arm assembly according to claim 1, wherein the handle mechanism further comprises a slotted rod connected between the end of the cable and a threaded anchor.

14. The universal arm assembly according to claim 13, wherein the slotted rod is connected to the threaded anchor with at least one threaded movable bearing.

15. The universal arm assembly according to claim 13, wherein the at least one shaft is positioned within a slot of the slotted rod, wherein the slotted rod is positioned substantially perpendicular to a length of the at least one shaft.

* * * * *